United States Patent [19]
Tran et al.

[11] Patent Number: 5,716,403
[45] Date of Patent: Feb. 10, 1998

[54] SINGLE PIECE FOLDABLE INTRAOCULAR LENS

[75] Inventors: Son Trung Tran, Arlington; Stephen J. Van Noy, Fort Worth, both of Tex.

[73] Assignee: Alcon Laboratories, Inc., Fort Worth, Tex.

[21] Appl. No.: 567,972

[22] Filed: Dec. 6, 1995

[51] Int. Cl.$^6$ .................................................... A61F 2/16
[52] U.S. Cl. ........................................................... 623/6
[58] Field of Search .................................................. 623/6

[56] References Cited

U.S. PATENT DOCUMENTS

| | | |
|---|---|---|
| 4,174,543 | 11/1979 | Kelman . |
| 4,251,887 | 2/1981 | Anis . |
| 4,268,921 | 5/1981 | Kelman . |
| 4,568,347 | 2/1986 | Reichert, Jr. ................ 623/6 |
| 4,664,666 | 5/1987 | Barrett . |
| 4,710,195 | 12/1987 | Giovinazzo .................. 623/6 |
| 4,725,277 | 2/1988 | Bissonette . |
| 4,804,361 | 2/1989 | Anis . |
| 4,834,750 | 5/1989 | Gupta . |
| 4,878,911 | 11/1989 | Anis . |
| 4,923,468 | 5/1990 | Wild . |
| 4,990,159 | 2/1991 | Kraff ............................ 623/6 |
| 5,071,432 | 12/1991 | Baikoff ......................... 623/6 |
| 5,118,452 | 6/1992 | Lindsey et al. . |
| 5,133,749 | 7/1992 | Nordan ......................... 623/6 |
| 5,141,507 | 8/1992 | Parekh . |
| 5,171,268 | 12/1992 | Ting et al. . |
| 5,180,390 | 1/1993 | Drews . |
| 5,185,107 | 2/1993 | Blake . |
| 5,197,981 | 3/1993 | Southard ....................... 623/6 |
| 5,236,970 | 8/1993 | Christ et al. . |
| 5,266,241 | 11/1993 | Parekh . |
| 5,306,297 | 4/1994 | Rheinish et al. . |
| 5,359,021 | 10/1994 | Weinschenk, III et al. . |
| 5,403,901 | 4/1995 | Namdaran et al. . |
| 5,411,553 | 5/1995 | Gerace et al. . |

FOREIGN PATENT DOCUMENTS

| | | |
|---|---|---|
| 0 215 468 A2 | 3/1987 | European Pat. Off. . |
| 0 215 468 A3 | 3/1987 | European Pat. Off. . |
| 0 566 461 A1 | 10/1993 | European Pat. Off. . |
| 2581535 | 11/1986 | France . |
| 2111835 | 7/1983 | United Kingdom . |

*Primary Examiner*—Randy C. Shay
*Attorney, Agent, or Firm*—Jeffrey S. Schira

[57] ABSTRACT

A single piece soft foldable IOL having open loop haptics of specific thickness and geometry. The unique geometry provides an IOL with improved fixation and centration.

4 Claims, 2 Drawing Sheets

SINGLE PIECE FOLDABLE INTRAOCULAR LENS

BACKGROUND OF THE INVENTION

This invention relates generally to the field of intraocular lenses (IOLs) and, more particularly, to foldable IOLs.

The human eye in its simplest terms functions to provide vision by transmitting light through a clear outer portion called the cornea, and focusing the image by way of a lens onto a retina. The quality of the focused image depends on many factors including the size and shape of the eye, and the transparency of the cornea and lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an IOL.

The surgical incision in the globe used to remove the natural lens and to insert the IOL can distort the spherical shape of the cornea, thereby causing the cornea to be longer in one direction. Surgically induced astigmatic changes to the eye can be reduced by minimizing the size of the incision. To permit the IOL to be inserted through a smaller incision, soft, foldable IOLs have been developed. These IOLs generally are made from biocompatible hydrogel, silicone or acrylic (see e.g., U.S. Pat. Nos. 5,411,553 (Gerace, et al.), 5,403,901 (Namdaran, et al.), 5,359,021 (Weinschenk, III, et al.), 5,236,970 (Christ, et al.), 5,141,507 (Parekh) and 4,834,750 (Gupta) the entire contents of which are incorporated herein by reference).

Prior to the present invention, sort, foldable IOLs were of a multi-piece design, with the optic made from the foldable material, and the haptics made from somewhat more rigid polypropylene or polymethylmethacrylate (PMMA) so as to provide the necessary fixation and centration of the IOL. The use of polypropylene or PMMA haptics requires somewhat difficult and expensive methods for attaching the haptics to the optic (see, e.g., U.S. Pat. Nos. 5,306,297 (Rheinish, et al.), 5,266,241 (Parekh), 5,185,107 (Blake), 5,171,268 (Ting et al.) and 5,118,452 (Lindsey, et al.) the contents of which are incorporated herein by reference).

In addition, the centration force exerted by haptics made from thermoplastic, non-cross-linked materials such as polypropylene or PMMA tends to decay over time ("stress relaxation"), particularly at normal body temperature (approximately 35° C.), because these materials exhibit plastic, rather than elastic, deformation. To compensate for force decay and avoid decentration over time, non-cross-linked thermoplastic haptics need to exert higher centration forces initially so that adequate centration force is preserved over time. Thermoset, cross-linked materials such as hydrogel, silicone or acrylic exhibit elastic deformation at normal body temperature and therefore, do not relax to the same degree as non-cross-linked, thermoplastic materials. As a result, the initial centration force required for haptics made from these thermoset, cross-linked materials does not need to compensate for decay and may be much lower initially.

Prior to the present invention, however, single piece soft IOLs designs have been limited to plate designs (see e.g., U.S. Pat. No. 4,664,666 (Barrett) the contents of which is incorporated herein by reference) or encircling haptic design (see e.g., U.S. Pat. Nos. 4,251,887, 4,804,361, 4,878,911 (all to Anis) and 5,180,390 (Drews) the contents of which are incorporated herein by reference). Plate designs may not offer the centration and fixation benefits of open loops haptic designs. The encircling haptic design was thought necessary to provide sufficient support for the optic when the haptic was made from the relatively flaccid hydrogel, silicone or acrylic materials. Although the encircling haptic design may be used, the additional haptic material adds to the volume to the IOL that must be inserted through the incision, requiring the incision size to be increased.

Therefore, a need continues to exist for a single piece, soft, foldable IOL with an open loop haptic design.

BRIEF SUMMARY OF THE INVENTION

The present invention improves upon the prior art by providing a single piece soft foldable IOL having open loop haptics of specific thickness and geometry. The unique geometry provides an IOL with improved fixation and centration.

Accordingly, one objective of the present invention is to provide a single piece soft, foldable IOL.

Another objective of the present invention is to provide a single piece soft, foldable IOL with an open loop haptic design.

Still another objective of the present invention is to provide a soft, foldable IOL wherein the haptics are made from the same material as the optic.

These and other advantages and objectives of the present invention will become apparent from the detailed description and claims that follow.

Figure 1:
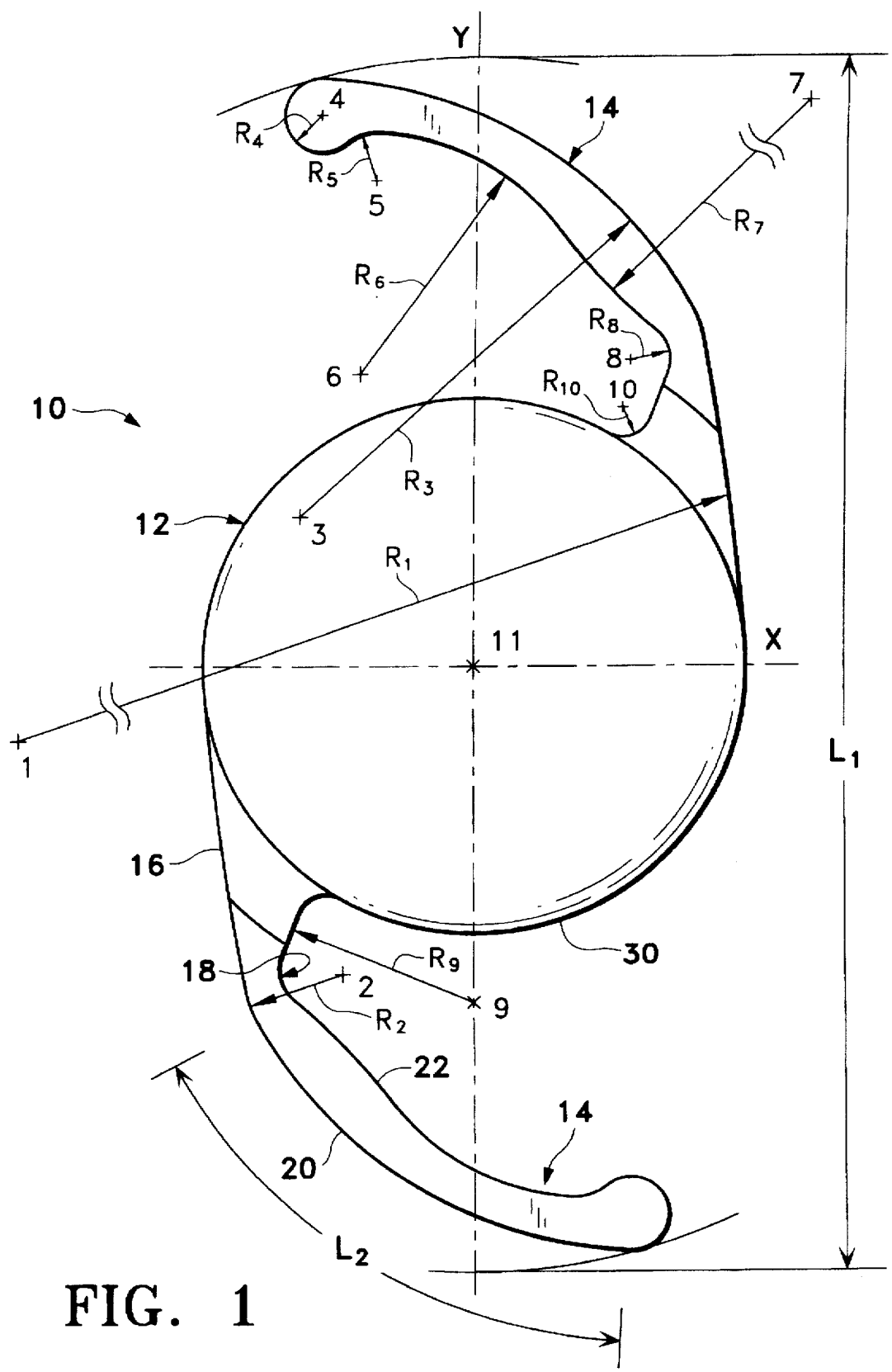
FIG. 1 is a plan view of the IOL of the present invention.

FI. 2 is a cross-section view of the IOL of the present invention taken along the Y-axis in FIG. 1.

DETAILED DESCRIPTION OF THE INVENTION

IOL 10 of the present invention generally includes optic 12 and at least two haptics 14. IOL 10 may have an overall length $L_1$ of any suitable dimension, with between 10.5 millimeters (mm) and 14.0 mm being preferred and 12.5 mm being most preferred. Optic 12 and haptics 14 are molded in a single piece from the same material. The material used to make IOL 10 may be any soft biocompatible material capable of being folded. Suitable materials are the hydrogel, silicone or acrylic materials described in U.S. Pat. Nos. 5,411,553 (Gerace, et al.), 5,403,901 (Namdaran, et al.), 5,359,021 (Weinschenk, III, et al.), 5,236,970 (Christ, et al.), 5,141,507 (Parekh) and 4,834,750 (Gupta). Optic 12 has an anterior side 24 and a posterior side 26 and may be of any suitable diameter, with between 4.5 mm and 7.0 mm being preferred and 5.5 mm being most preferred. Optic 12 may also be elliptical or oval. The thickness of optic 12 will vary depending on the dioptic power desired and the index of refraction for the material used, but generally will be between 0.4 mm and 1.5 mm. The principal design criteria for IOL 10 is to maximize the diameter of optic 12 while minimizing the size of the surgical incision. The material used to make optic 12 may be modified to absorb ultraviolet radiation, or any other desired radiation wavelength.

Figure 2:
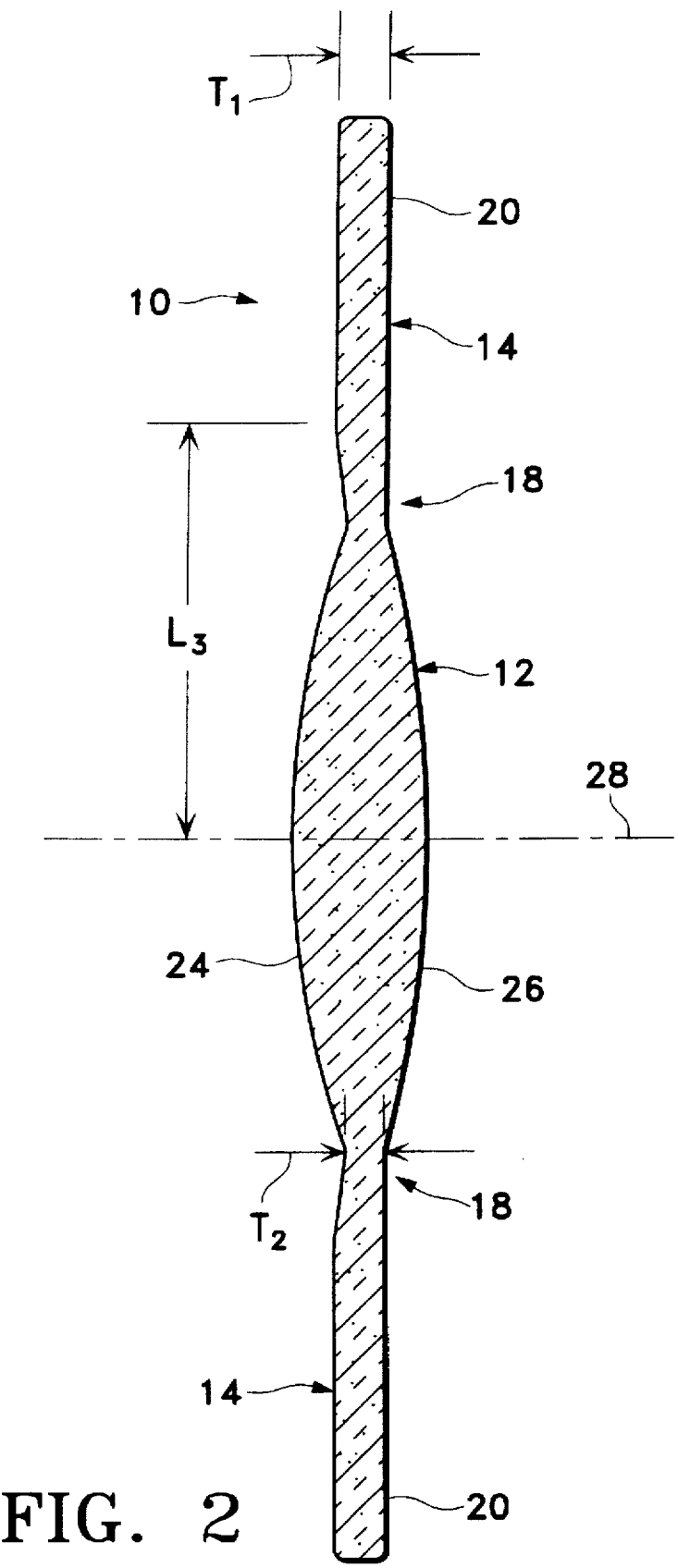

Haptics 14 contain gusset 16, elbow 18 and distal portion 20 having widened portion 22. As best seen in FIG. 2, the thickness $T_1$ of elbow 18 and distal portion 20 of haptic 14 is uniform, and preferably between about 0.30 mm and 0.60 mm, with between about 0.40 mm and 0.50 mm being more preferred and about 0.43 being most preferred. Gusset 16, however, has a thickness $T_2$ that is reduced toward anterior side 24 of optic 12. Gusset 16 preferably is between about 0.15 mm and 0.60 mm thick, with between about 0.25 mm and 0.35 mm thick being more preferred and about 0.30 mm being most preferred. This reduced thickness generally extends from edge 30 of optic 12 to a distance $L_3$ from optical axis 28, preferably between 3.0 mm and 4.5 mm with 3.5 mm being most preferred. The relatively thin cross section of gusset 16 and edge 30 provides a thinner profile when IOL 10 is inserted through the surgical incision, and reducing the thickness of gusset 16 on anterior side 24 of optic 12 helps to ensure that any vaulting of optic 12 will occur posteriorly. The reduced thickness of gusset 16 also facilitates fluid circulation (e.g., viscoelastic) between posterior side 26 and anterior side 24 of IOL 10. Alternatively, gusset 16 or optic 12 may be provided with other means (such as holes, grooves, notches, micro-fenestration, or protuberances (all not shown)) to facilitate fluid flow between posterior side 26 and anterior side 24 of IOL 10. Distal portion 20 may have a length $L_2$ of any suitable dimension, but between 4.00 mm and 5.00 mm is preferred with 4.65 mm being most preferred. The relatively long length and radius of distal portion 20 provides greater contact with the capsular bag for better fixation when IOL 10 is implanted in the eye. Elbow 18 creates a hinge allowing haptic 14 to flex while minimizing buckling and vaulting of optic 12. Widened portion 22 increases the stiffness of haptic 14 just past elbow 18, thereby increasing the strength of haptic 14 at a critical stress point.

The preferred radii $R_1$–$R_{10}$ used to construct IOL 10 are set forth below:

| Radius | Preferred Length (mm) | Most Preferred Length (mm) |
| --- | --- | --- |
| $R_1$ | 29.0–31.0 | 30.0 |
| $R_2$ | 0.5–3.0 | 1.0 |
| $R_3$ | 4.0–5.0 | 4.5 |
| $R_4$ | 0.25–0.50 | 0.38 |
| $R_5$ | 0.25–0.75 | 0.50 |
| $R_6$ | 2.0–3.0 | 2.5 |
| $R_7$ | 5.0–7.0 | 6.0 |
| $R_8$ | 0.15–1.00 | 0.40 |
| $R_9$ | 1.0–3.0 | 2.0 |
| $R_{10}$ | 0.20–0.40 | 0.30 |

The above radii are measured from the following corresponding construction points:

| Point | X Coordinate (mm) | Y Coordinate (mm) |
| --- | --- | --- |
| 1 | −27.152 | −2.304 |
| 2 | −1.322 | −3.191 |
| 3 | −1.763 | 1.538 |
| 4 | −1.577 | 5.659 |
| 5 | −1.016 | 4.988 |
| 6 | −1.157 | 2.993 |
| 7 | 5.672 | 8.054 |
| 8 | 1.576 | 3.136 |
| 9 | −0.014 | −3.481 |
| 10 | 1.500 | 2.656 |
| 11 | 0.000 | 0.000 |

This description is given for purposes of illustration and explanation. It will be apparent to those skilled in the relevant art that changes and modifications may be made to the invention described above without departing from its scope or spirit.

We claim:

1. An intraocular lens, comprising:

a) an optic made from a foldable material; and b) at least two haptics integrally made with the optic, each haptic having i) a gusset at the intersection of the haptic and the optic, the gusset being between approximately 0.25 millimeters and 0.35 millimeters thick in cross section, ii) a distal portion having a widened portion, the distal portion being thicker than the gusset and between approximately 0.30 millimeters and 0.60 millimeters thick in cross section and iii) a hinge-forming elbow spaced intermediate the gusset and the widened portion, the elbow sized and shaped to allow the haptic to flex while minimizing buckling and vaulting of the optic, the elbow being thicker than the gusset and between approximately 0.30 millimeters and 0.60 millimeters thick in cross section.

2. The intraocular lens of claim 1 wherein the foldable material is selected from the group consisting of hydrogels, silicones and acrylics.

3. The intraocular lens of claim 1 wherein the distal portion has an overall length of between approximately 4.0 millimeters an 5.0 millimeters.

4. The intraocular lens of claim 1 wherein the foldable material is an acrylic.

* * * * *